(12) United States Patent
Qian

(10) Patent No.: US 9,139,859 B2
(45) Date of Patent: Sep. 22, 2015

(54) METHOD FOR PREPARING (R)-PRAZIQUANTEL

(71) Applicant: TONGLI BIOMEDICAL CO., LTD, Suzhou, Jiangsu Province (CN)

(72) Inventor: Mingxin Qian, Suzhou (CN)

(73) Assignee: TONGLI BIOMEDICAL CO., LTD, Suzhou (CN)

( * ) Notice: Subject to any disclaimer, the term of this patent is extended or adjusted under 35 U.S.C. 154(b) by 0 days.

(21) Appl. No.: 14/471,652

(22) Filed: Aug. 28, 2014

(65) Prior Publication Data

US 2014/0370555 A1 Dec. 18, 2014

Related U.S. Application Data

(63) Continuation of application No. PCT/CN2013/072028, filed on Feb. 28, 2013.

(30) Foreign Application Priority Data

Feb. 28, 2012 (CN) .......................... 2012 1 0046090

(51) Int. Cl.
| | |
|---|---|
| C07D 471/04 | (2006.01) |
| C07D 217/14 | (2006.01) |
| C12P 41/00 | (2006.01) |
| C07D 211/60 | (2006.01) |
| C07B 53/00 | (2006.01) |
| C07D 217/16 | (2006.01) |
| C07D 217/26 | (2006.01) |
| C12P 17/12 | (2006.01) |
| C12P 17/18 | (2006.01) |

(52) U.S. Cl.
CPC ................ *C12P 41/00* (2013.01); *C07B 53/00* (2013.01); *C07D 211/60* (2013.01); *C07D 217/14* (2013.01); *C07D 217/16* (2013.01); *C07D 217/26* (2013.01); *C07D 471/04* (2013.01); *C12P 17/12* (2013.01); *C12P 17/182* (2013.01); *C12P 41/004* (2013.01)

(58) Field of Classification Search
None
See application file for complete search history.

(56) References Cited

U.S. PATENT DOCUMENTS

| 4,497,952 A | 2/1985 | Kim et al. |
| 2014/0370556 A1 | 12/2014 | Qian |

FOREIGN PATENT DOCUMENTS

CN 102093346 6/2011

OTHER PUBLICATIONS

Roszkowski, P., et al., Enantioselective synthesis of (R)-(–)-praziquantel (PZQ), Tetrahedron: Asymmetry, vol. 17, No. 9, 2006, pp. 1415-1419, see p. 1416.
Ma, Chen, et al., Total synthesis of (–)-praziquantel: an anthelmintic drug, Journal of Chemical Research, 2004, No. 3, pp. 186-197, see 186.

*Primary Examiner* — Zinna Northington Davis
(74) *Attorney, Agent, or Firm* — Stites & Harbison PLLC; Cong Ding

(57) ABSTRACT

The invention relates to a new method for preparing (R)-praziquantel. In the invention, by taking advantage of the high stereo selectivity, site selectivity and region selectivity of an enzyme, an intermediate of a pure optical and chiral (R)-praziquantel are obtained by means of the dynamic kinetic resolution of an enantiomer from the synthesized racemate or derivatives thereof, and the (R)-praziquantel is obtained by using various conventional and mature organic chemical reactions with higher yield. The method of the invention has the potential advantages of easily available raw materials, low cost, environmentally safer process and convenience for large-scale production. Also, the purity of the end product can be more than 98%. By adopting the invention, the quality of the product is improved and a basis for developing high quality of active pharmaceutical ingredients and formulations is established, and thus the pending industrial problem of purifying praziquantel over 30 years becomes solvable.

10 Claims, No Drawings

METHOD FOR PREPARING (R)-PRAZIQUANTEL

CROSS-REFERENCES TO RELATED APPLICATIONS

This application is a continuation application of PCT Patent Application No. PCT/CN2013/072028, filed Feb. 28, 2013, which claims priority to CN201210046090.9 filed Feb. 28, 2012; the disclosures of each is hereby incorporated by reference in its entirety and for all purposes.

FIELD OF THE INVENTION

The present invention relates to a method for preparing (R)-praziquantel.

DESCRIPTION OF THE RELATED ART

Praziquantel is a broad spectrum antiparasitic drug and a racemic mixture. It has a wide anthelmintic activity on *Schistosoma japonica, Schistosoma haematobium, Schistosoma mansoni* and the like. Furthermore, praziquantel also has activity against *Paragonimus westermani, Clonorchis sinensis, Echinococcus, Cysticercus, Sparganosis mansoni, Fasciolopsis, Cestode* and the like. In addition, praziquantel has the advantages of high efficacy, short course of treatment, small dose, fast metabolism, low toxicity and convenient oral administration. Thus, the discovery of praziquantel is a major breakthrough on chemotherapy of parasitic diseases, and praziquantel has become a drug of choice for treatment of various helminthiases Praziquantel was firstly synthesized by Seubert at al. in 1975, and was developed as a drug by the two pharmaceuticals companies, Merck KGaA and Bayer AG. In 1980, praziquantel was firstly on the market under the trade name of Cesol, and now it has been used extensively in the world. Besides for human therapy, praziquantel is also broadly used for treatment of parasitic diseases in animals including poultries or the like. However, in the conventional manufacture processes for preparing praziquantel, usually some toxic and harmful chemicals, such as potassium cyanide and cyclohexanecarboxylic acid chloride, are needed and a longer process route and a relative harsh reaction condition are used (see the following scheme).

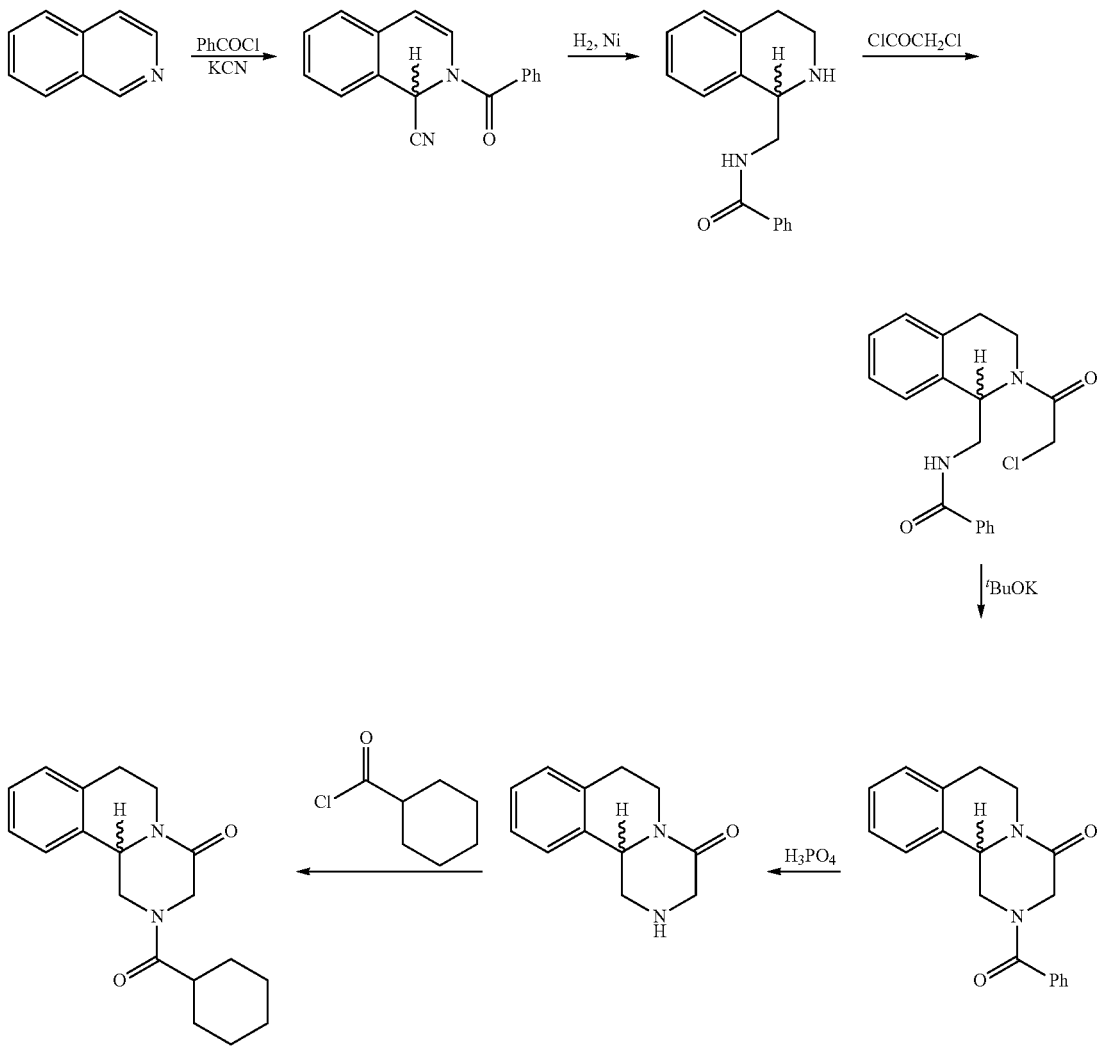

In early 1980, two optical isomers, (R)-praziquantel and (S)-praziquantel, are obtained from synthesized praziquantel using resolution by some researchers. It has been found from the pre-clinical studies and preliminary clinical trials that: (R)-praziquantel is an active isomer in praziquantel while (S)-praziquantel is an inactive and even harmful component. At the same dosage, (R)-praziquantel has a better clinical efficacy than praziquantel. Alternatively, it has been desired and proposed to develop (R)-praziquantel by the World Health Organization. However, over the years the technical problem of low yield on synthesizing (R)-praziquantel is still unsolvable.

SUMMARY OF THE INVENTION

A technical problem to be solved by the invention is to provide a method for preparing (R)-praziquantel with an environmentally safer process and a high yield. In order to solve the above technical problem, in one aspect, the invention provides a method for preparing (R)-praziquantel using the following reaction scheme:

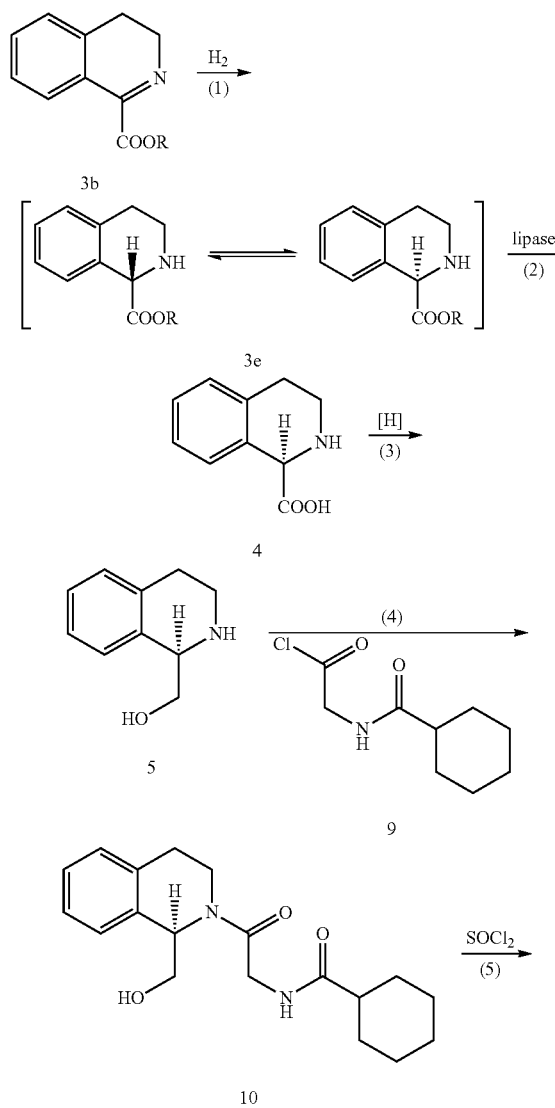

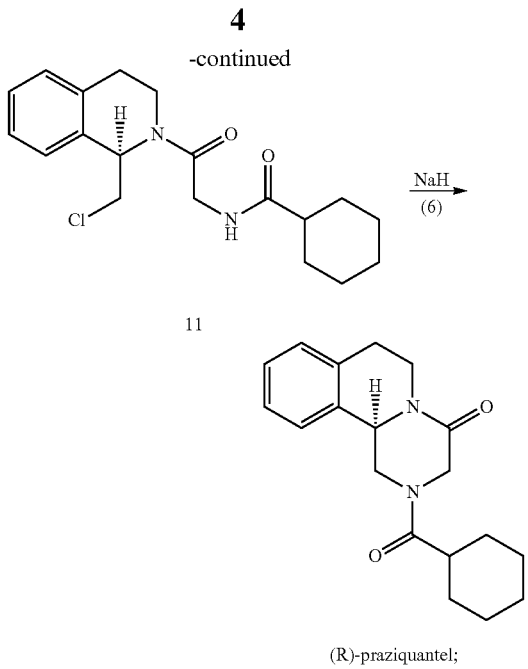

wherein
R represents alkyl; and wherein
in step (2), the lipase stereo-selectively hydrolyzes a (R)-tetrahydroisoquinoline formate of the racemic compound 3e to get a pure optical (R)-tetrahydroisoquinoline formic acid having the structure of compound 4.

Preferably, in the step (2), the lipase is selected from the group consisting of *Candida Rugosa* Lipase, *Candida Antarctica* Lipase A (CAL-A) and *Candida Antarctica* Lipase B (CAL-B, Novozyme 435). According to the invention, the used enzymes are not limited to natural sources, and may be the enzymes recombined by means of molecular biological methods. Furthermore, the used enzyme is not limited to a certain form, for example, it may be a dry powder or also may be immobilized.

Preferably, R is selected from the group consisting of methyl, ethyl, isopropyl, tert-butyl or p-methoxyphenyl, and more preferably isopropyl, tert-butyl and p-methoxyphenyl.

More preferably, in the step (2), the racemic compound 3e is reacted with the lipase in a water-saturated ionic liquid in the presence of a base at 0-50° C., to obtain the compound 4.

Still more preferably, in the step (2) the reaction temperature is 25-50° C.

In a particular embodiment, in the step (2), the ionic liquid may be various ionic liquids suitable for as a solvent, and preferably 1-n-butyl-3-methylimidazolium tetrafluoroborate, 1-n-butyl-3-methylimidazolium hexafluorophosphate, 1-n-butyl-3-methylimidazolium bis[(trifluoromethyl)sulfonyl]imide or 1-n-butyl-pyridinium hexafluorophosphate.

Preferably, in the step (2), the base is selected from the group consisting of tetrabutyl ammonium hydroxide, pyridine, sodium bicarbonate, triethylamine or any combination thereof, and wherein the mole ratio of the base to the racemic compound 3e is in the range of 1-1.1:1, for example 1.05:1. More preferably, the base is tetrabutyl ammonium hydroxide.

In a specific embodiment, the step (2) can be implemented as follows: the racemic compound 3e, the water-saturated ionic liquid and the base are added into a membrane reactor and stirred evenly, and the lipase is added to start the reaction under a sealed condition, and wherein the reaction is monitored by HPLC.

More preferably, the molecular weight cutoff of the ultrafiltration membrane in the membrane reactor is 10000 Da. After the reaction is ended, the components except the lipase in the reaction mixture are extruded out using a gas, so that the lipase is retained in the membrane reactor for synthesizing a next batch of (R)-praziquantel.

In another specific embodiment, in the step (1), the compound 3b is reacted with $H_2$ in the presence of a Pd/C catalyst or a Raney nickel catalyst at 60-70° C. When the reaction is ended, the catalyst is recycled by filtering, and the filtrate is concentrated under reduced pressure to get the racemic compound 3e.

Preferably, the step (3) can be implemented as follows: the compound 4 is suspended in tetrahydrofuran after it is previously converted into its hydrochloride form, and the solution is cooled to 0-5° C. and a solution of borane in tetrahydrofuran is added dropwise, subsequently after the addition the reaction is performed at 20-25° C. When the reaction is completed, the reaction mixture is cooled to 0-5° C. and methanol is added, subsequently 10 wt %-15 wt % of sodium hydroxide solution is added dropwise at 0-5° C., and after the addition the reaction mixture is heated to 20-25° C. to perform neutralization reaction. When the neutralization reaction is completed the organic solvent is evaporated off under reduced pressure, and subsequently the residue is extracted by dichloromethane and the dichloromethane phase is dried over anhydrous sodium sulfate and concentrated to get crude product, and finally the crude product is recrystallized with toluene to get the compound 5.

Or alternatively, the step (3) also can be implemented as follows: the compound 4 is suspended in tetrahydrofuran after it is previously converted into its hydrochloride form, and the solution is cooled to 0-5° C., subsequently sodium borohydride is added and then the solution of boron trifluoride etherate is added dropwise, and then after the addition the reaction is performed at 20-25° C. When the reaction is completed, the reaction mixture is cooled to 0-5° C. and methanol is added, subsequently 10 wt %-15 wt % of sodium hydroxide solution is added dropwise at 0-5° C., and after the addition the reaction mixture is heated to 20-25° C. to perform neutralization reaction. When the neutralization reaction is completed the organic solvent is evaporated off under reduced pressure, and subsequently the residue is extracted by dichloromethane and the dichloromethane phase is dried over anhydrous sodium sulfate and concentrated to get crude product, and finally the crude product is recrystallized with toluene to get the compound 5.

The compound 4 is added to tetrahydrofuran and sodium borohydride is added, and the boron trifluoride etherate is added dropwise, and the mixture is stirred at 20-25° C. When the reaction is completed, the reaction mixture is cooled to 0-5° C. and methanol is added, subsequently 10 wt %-15 wt % of sodium hydroxide solution is added dropwise at 0-5° C., and after the addition the reaction mixture is heated to 20-25° C. to perform neutralization reaction. When the neutralization reaction is completed, the organic solvent is evaporated off under reduced pressure, and subsequently the residue is extracted by dichloromethane and the organic phase is dried over anhydrous sodium sulfate and concentrated to get crude product, and finally the crude product is recrystallized with toluene to get the compound 5.

Preferably, the step (6) can be implemented as follows: the compound 11 and tetrahydrofuran are added into a reactor and stirred evenly, and sodium hydride is added to the mixture in batches, after the addition the mixture is stirred for 3-4 hours at room temperature, and heated to 75-80° C. and stirred for further 5-7 hours. When HPLC indicates the completion of reaction, the reaction mixture is poured into saturated salt water to quench the reaction and separate out the product, and crude product is gained by filtering and recrystallized with anhydrous ethanol to get (R)-praziquantel.

The steps (4) and (5) according to the above technical solution of the invention are well known for a person skilled in the art, and they will be illustrated hereinafter in connection with embodiments and thus will not be described in more detail here.

In another aspect, the invention provides an immediate of (R)-praziquantel, having the general formula I:

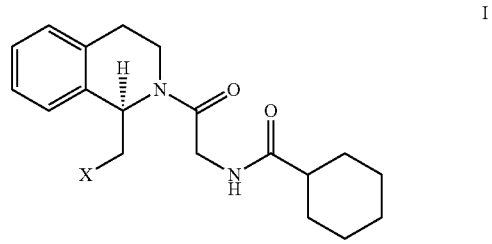

Wherein X represents OH or Cl.

By adopting the above technical solutions, as compared with the prior art the invention has the following advantages:

The invention is applicable for large-scale industrial production through the synthesis route using bio-enzyme catalysis. In the method of the invention, by taking advantage of the high stereo-selectivity, site selectivity and region selectivity of an enzyme, an intermediate (R)-compound 4 of a pure optical and chiral (R)-praziquantel are obtained by means of the dynamic kinetic resolution of an enantiomer of the synthesized racemate or derivatives thereof. The method of the invention has the potential advantages of mature yet environmentally improved process, easily available raw materials and low cost. Accordingly, the method of the invention is conveniently adoptable for large-scale production of (R)-praziquantel with an improved quality. In the invention, the purity of the product can be more than 98%. These improvements will lay a foundation for further development of high-quality active pharmaceutical ingredients and pharmaceutical formulations, and make the pending industrial problem of separation and purification of high purity of (R)-praziquantel over the past 30 years solvable.

In the invention, the bio-enzyme catalysis is utilized as a core technology to develop a high yield and environmentally safer process for chiral synthesis of (R)-praziquantel. This will pave the way for further preclinical and clinical evaluation, large-scale manufacturing and eventually entering international market of (R)-praziquantel.

DESCRIPTION OF THE PREFERRED EMBODIMENTS

The invention will be further detailedly illustrated in connection with specific embodiments, however, the invention is not limited to the following embodiments.

EMBODIMENT 1

Synthesis of Tetrahydroisoquinoline Formate Using the Following Reaction Scheme:

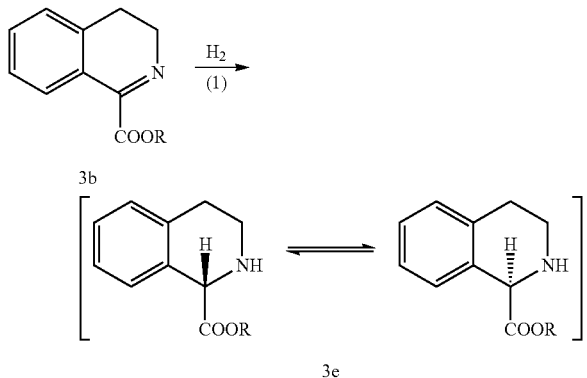

Wherein R represents methyl, ethyl, isopropyl, tert-butyl or p-methoxyphenyl.

EXAMPLE 1-1

To a sealed vessel dihydro isoquinoline methyl formate (756.8 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 749.6 g oily compound of tetrahydroisoquinoline methyl formate (hereinafter known as compound 3e-1), and the purity of the compound was 95% and the yield was 98%.

The NMR data of the compound 3e-1 was as follows:
$^1$H NMR (CDCl$_3$, 400 MHz, δ ppm): 1.35 (s, 3H, CH$_3$), 2.03-2.21 (brs, 1H), 2.68-2.74 (m, 2H), 2.98-3.01 (t, J=5.9 Hz, 2H), 4.54 (s, 1H), 7.02-7.40 (m, 4H, ArH).

EXAMPLE 1-2

To a sealed vessel dihydro isoquinoline ethyl formate (812.9 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 804.58 g oily compound of tetrahydroisoquinoline ethyl formate (hereinafter known as compound 3e-2), and the purity of the compound was 96% and the yield was 98%.

The NMR data of the compound 3e-2 was as follows:
$^1$H NMR (CDCl$_3$, 400 MHz, δ ppm): 1.28-1.37 (t, 3H, —CH$_2$—CH$_3$), 2.01-2.27 (br s, 1H, NH), 2.78-2.84 (m, 2H, CH$_2$), 3.03-3.33 (m, 2H, CH$_2$), 4.19-4.24 (m, 2H, —CH$_2$—CH$_3$), 4.71 (s, 1H, CH), 7.11-7.35 (m, 4H, ArH).

EXAMPLE 1-3

To a sealed vessel dihydro isoquinoline isopropyl formate (869.0 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 914.57 g oily compound of tetrahydroisoquinoline isopropyl formate (hereinafter known as compound 3e-3), and the purity of the compound was 94% and the yield was 98%.

The NMR data of the compound 3e-3 was as follows:
$^1$H NMR (CDCl$_3$, 400 MHz, δ ppm): 1.28-1.35 (t, 3H×2, CH$_3$), 2.03-2.22 (brs, 1H, NH), 2.67-2.69 (m, 2H, CH$_2$), 2.83-2.93 (m, 2H, CH$_2$), 4.31-4.54 (m, 1H, —CH—CH$_3$), 4.74 (s, 1H, CH), 7.02-7.32 (m, 4H, ArH).

EXAMPLE 1-4

To a sealed vessel dihydro isoquinoline tertbutyl formate (925.2 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture is heated to 65° C. and stirred for 24 hours. When analysis indicated the completion of the reaction, the catalyst was recycled by filtering, and the filtrate was concentrated under reduced pressure to get 895.91 g oily compound of tetrahydroisoquinoline tertbutyl formate (hereinafter known as compound 3e-4), and the purity of the compound was 96% and the yield was 96%.

The NMR data of the compound 3e-4 was as follows:
$^1$H NMR (CDCl$_3$, 400 MHz, δ ppm): 1.48 (s, 9H, CH$_3$), 2.10-2.35 (br s, 1H, NH), 2.61-2.84 (m, 2H, CH$_2$), 2.97-3.08 (m, 2H, CH$_2$), 3.08 (s, 3H, CH$_3$), 4.78 (s, 1H, CH), 7.12-7.43 (m, 4H, ArH).

EXAMPLE 1-5

To a sealed vessel dihydro isoquinoline p-methoxyphenyl formate (1170.2 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 1131.13 g solid compound of tetrahydroisoquinoline p-methoxyphenyl formate (hereinafter known as compound 3e-5), and the purity of the compound was 93% and the yield was 96%.

The NMR data of the compound 3e-5 was as follows:
$^1$H NMR (CDCl$_3$, 400 MHz, δ ppm): 2.04-2.35 (br s, 1H, NH), 2.66-2.74 (m, 2H, CH$_2$), 2.87-3.02 (m, 2H, CH$_2$), 3.08 (s, 3H, CH$_3$), 4.76 (s, 1H, CH), 7.02-7.13 (m, 4H, ArH), 7.20-7.31 (m, 2H, ArH), 8.16-8.28 (m, 2H, ArH).

EXAMPLE 1-6

To a sealed vessel dihydro isoquinoline methyl formate (756.8 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 726.6 g oily compound of tetrahydroisoquinoline methyl formate (compound 3e-1, the purity was 95.5%, and the yield was 95%), and this compound can be directly used in the next step without further purification.

EXAMPLE 1-7

To a sealed vessel dihydro isoquinoline ethyl formate (812.9 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 788.2 g oily compound of tetrahydroisoquinoline ethyl formate (compound 3e-2, the purity was 96.8% and the yield was 96%), and this compound can be directly used in the next step without further purification.

EXAMPLE 1-8

To a sealed vessel dihydro isoquinoline isopropyl formate (869.0 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 859.9 g oily compound of tetrahydroisoquinoline isopropyl formate (compound 3e-3, the purity was 95.4% and the yield was 98%), and this compound can be directly used in the next step without further purification.

EXAMPLE 1-9

To a sealed vessel dihydro isoquinoline tertbutyl formate (925.2 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 895.9 g oily compound of tetrahydroisoquinoline tertbutyl formate (compound 3e-4, the purity was 96.6% and the yield was 96%), and this compound can be directly used in the next step without further purification.

EXAMPLE 1-10

To a sealed vessel dihydro isoquinoline p-methoxyphenyl formate (1170.2 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 1131.13 g solid compound of tetrahydroisoquinoline p-methoxyphenyl formate (compound 3e-5, the purity was 95.2% and yield was 96%), and this compound can be directly used in the next step without further purification.

Embodiment 2

Synthesis of (R)-Tetrahydroisoquinoline Formic Acid (Compound 4) Using the Following Reaction Scheme

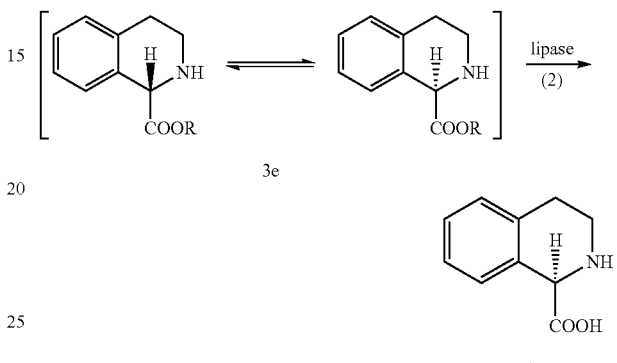

EXAMPLE 2-1

Experiments for Reaction Mediums

To a 50 ml of membrane reactor (the molecular weight cutoff of the ultrafiltration membrane is 10000 Da) 205.3 mg (100 mmol) of racemic tetrahydroisoquinoline ethyl formate (±3e-2), 20 ml of water-saturated ionic liquid and 272.5 mg (105 mmol) tetrabutyl ammonium hydroxide were added and stirred evenly, and 100 mg of *Candida Antarctica* lipase B (available from Sigma) was added, subsequently the reaction was started under a sealed condition (at 20° C. and 180 r/min) with HPLC monitoring the reaction. The reaction was ended 24 hours later, and the reaction mixture (including the substrates and product) were extruded out using $N_2$ from the membrane reactor and the *Candida Antarctica* lipase B was retained in the reactor. In repeated batch reactions, 205.3 mg (100 mmol) of racemic tetrahydroisoquinoline ethyl formate (±3e-2), 20 ml of water-saturated ionic liquid and 272.5 mg (105 mmol) tetrabutyl ammonium hydroxide were added respectively to the reactor to perform a next batch reaction. The used ionic liquids and the corresponding conversion and optical purity in different batches are shown in the following table 1.

TABLE 1

| No. | abbreviation | ionic liquid | conversion (24 hours) | ee value (24 hours) |
|---|---|---|---|---|
| 1 | ($C_4$mim)$BF_4$ | 1-n-butyl-3-methylimidazolium tetrafluoro borate | 78% | 95% |
| 2 | ($C_4$mim)$PF_6$ | 1-n-butyl-3-methyliidazolium hexafluoro phosphate | 99% | 99% |

TABLE 1-continued

| No. | abbreviation | ionic liquid | conversion (24 hours) | ee value (24 hours) |
|---|---|---|---|---|
| 3 | $(C_4mim)(NTf_2)$ | 1-n-butyl-3-methylimidazolium bis[(trifluoromethyl)sulfonyl]imide | 99% | 99% |
| 4 | $(C_4Py)(PF_6)$ | 1-n-butyl-pyridinium hexafluorophosphate | 83% | 95% |

EXAMPLE 2-2

Experiments for Reaction Mediums

To a 50 ml of membrane reactor (the molecular weight cutoff of the ultrafiltration membrane is 10000 Da) 205.3 mg (100 mmol) of racemic tetrahydroisoquinoline ethyl formate (±3e-2), 20 ml of water-saturated ionic liquid and 272.5 mg (105 mmol) tetrabutyl ammonium hydroxide were added and stirred evenly, and 100 mg of *Candida rugosa*, lipase (available from Sigma) was added, subsequently the reaction was performed under a sealed condition (at 20° C. and 180 r/min) with HPLC monitoring the reaction. The reaction was ended 24 hours later, and the reaction mixture (including the substrates and product) were extruded out using $N_2$ from the membrane reactor and the *Candida rugosa* lipase was retained in the reactor. In repeated batch reactions, 205.3 mg (100 mmol) of racemic tetrahydroisoquinoline ethyl formate (±3e-2), 20 ml of water-saturated ionic liquid and 272.5 mg (105 mmol) tetrabutyl ammonium hydroxide were added respectively to the reactor to perform a next batch reaction. The used ionic liquids used and the corresponding conversion and optical purity in different batches are shown in the following table 2.

TABLE 2

| No. | abbreviation | ionic liquid | conversion (24 hours) | ee value (24 hours) |
|---|---|---|---|---|
| 1 | $(C_4mim)BF_4$ | 1-n-butyl-3-methylimidazolium tetrafluoro borate | 69.6% | 92.2% |
| 2 | $(C_4mim)PF_6$ | 1-n-butyl-3-methyliidazolium hexafluoro phosphate | 99.2% | 99.3% |
| 3 | $(C_4mim)(NTf_2)$ | 1-n-butyl-3-methylimidazolium bis[(trifluoromethyl)sulfonyl]imide | 99.1% | 99.2% |
| 4 | $(C_4Py)(PF_6)$ | 1-n-butyl-pyridinium hexafluorophosphate | 68.5% | 91.5% |

EXAMPLE 2-3

Experiments for Reaction Temperatures

To a 50 ml of membrane reactor (the molecular weight cutoff of the ultrafiltration membrane is 10000 Da) 205.3 mg (100 mmol) of racemic tetrahydroisoquinoline ethyl formate (±3e-2), 20 ml of water-saturated 1-n-butyl-3-methylimidazolium hexafluoro phosphate and 272.5 mg (105 mmol) tetrabutyl ammonium hydroxide were added and stirred evenly, and 100 mg of *Candida Antarctica* lipase B (available from Sigma) or *Candida rugosa* lipase (available from Sigma) was added, subsequently the reaction was started under a sealed condition (at 3° C., 25° C., 50° C. respectively for two sets of experiments, and 180 r/min) with HPLC monitoring the reaction. The reaction was ended 24 hours later, and the reaction mixture (including the substrates and product) were extruded out using $N_2$ from the membrane reactor and the *Candida Antarctica* lipase B or *Candida rugosa* lipase was retained in the reactor. In repeated batch reactions, 205.3 mg (100 mmol) of racemic tetrahydroisoquinoline ethyl formate (±3e-2), 20 ml of water-saturated 1-n-butyl-3-methylimidazolium hexafluoro phosphate and 272.5 mg (105 mmol) tetrabutyl ammonium hydroxide were added respectively to the reactor to perform a next batch reaction. The temperature, the used lipases, the corresponding conversion and optical purity in different batches are shown in the following table 3.

TABLE 3

| | enzyme | | | | | |
|---|---|---|---|---|---|---|
| | Candida Antarctica Lipase B | | | Candida Rugosa Lipase | | |
| temperature | conversion 12 hours | conversion 24 hours | ee value 24 hours | con version 12 hours | con version 24 hours | ee value 24 hours |
| 3° C. | 32% | 60.1% | 99% | 30.3% | 55.6% | 99% |
| 25° C. | 52.1% | 99.5% | 99.2% | 50.3% | 99.5% | 99.3% |
| 50° C. | 80.1% | 99.5% | 84.8% | 72.7% | 99.5% | 79.5% |

EXAMPLE 2-4

Experiments for Different Substrates

To a 50 ml of membrane reactor (the molecular weight cutoff of the ultrafiltration membrane is 10000 Da) 191.3 mg (100 mmol) of compound 3e-1, or 205.3 mg (100 mmol) of compound 3e-2, or 219.3 mg (100 mmol) of compound 3e-3, or 233.3 mg (100 mmol) of compound 3e-4, or 298.3 mg (100 mmol) of racemic tetrahydroisoquinoline p-methoxyphenyl formate (compound 3e-5), 20 ml of water-saturated 1-n-butyl-3-methylimidazolium hexafluoro phosphate and 272.5 mg (105 mmol) tetrabutyl ammonium hydroxide were added and stirred evenly, and 100 mg of *Candida Antarctica* lipase B (powder, available from Sigma) or *Candida rugosa* lipase (powder, available from Sigma) was added, subsequently the reaction was started under a sealed condition (at 25° C. respectively for two sets of experiments, and 180 r/min) with HPLC monitoring the reaction. The reaction was ended 24 hours later, and the reaction mixture (including the substrates and product) were extruded out from the membrane reactor using $N_2$ and the *Candida Antarctica* lipase B or *Candida rugosa* lipase was retained in the reactor. In repeated batch reactions, the corresponding compounds in certain amount, 20 ml of water-saturated 1-n-butyl-3-methylimidazolium hexafluoro phosphate and 272.5 mg (105 mmol) tetrabutyl ammonium hydroxide were respectively added to the reactor to perform a next batch reaction. The substrates, lipases, the corresponding conversion and optical purity in different batches are shown in the following table 4.

TABLE 4

| | enzyme | | | | | | | |
|---|---|---|---|---|---|---|---|---|
| | Candida Antarctica lipase B | | | | Candida Rugosa Lipase | | | |
| | The first enzyme reaction | | The fifth enzyme repeated reaction | | The first enzyme reaction | | The fifth enzyme repeated reaction | |
| substrate | conversion 24 hours | ee value 24 hours | conversion 24 hours | ee value 24 hours | conversion 24 hours | ee value 24 hours | conversion 24 hours | ee value 24 hours |
| methyl ester | 99.5% | 99.3% | 42.1% | 99.1% | 99.2% | 99.3% | 43.3% | 99.0% |
| ethyl ester | 99.4% | 99.6% | 50.1% | 99.0% | 99.3% | 99.6% | 51.5% | 99.0% |
| isopropyl ester | 99.3% | 99.5% | 99.1% | 99.1% | 99.5% | 99.2% | 99.3% | 99.1% |
| tertbutyl ester | 99.6% | 99.6% | 99.2% | 99.1% | 99.5% | 99.6% | 99.1% | 99.0% |
| p-methoxy phenyl ester | 99.5% | 99.2% | 99.1% | 99.2% | 99.3% | 99.2% | 99.2% | 99.1% |

EXAMPLE 2-5

Preparation of Compound 4

Experiments for preparing the reaction product (*Candida Rugosa* Lipae, powder, available from Sigma)

To a 10 L of membrane reactor (the molecular weight cutoff of the ultrafiltration membrane is 10000 Da) 466.6 g (2 mol) of racemic tertbutyl ester (compound 3e-4), 5 L of water saturated 1-n-butyl-3-methylimidazolium hexafluoro phosphate and 531.9 g (2.05 mol) tetrabutyl ammonium hydroxide were added and stirred evenly, and 100 g of *Candida Rugosa* Lipase (powder, available from Sigma) were added, subsequently the reaction was started under a sealed condition (at 20° C. and 180 r/min) with HPLC monitoring the reaction. The conversion was 99.6% 24 hours later and the reaction was ended. The reaction mixture liquid (including the substrates and product) were extruded out from the membrane reactor using $N_2$ and the *Candida Rugosa* Lipase was retained in the reactor. In repeated batch reactions, 466.6 g (2 mol) of compound 3e-4, 5 L of water-saturated 1-n-butyl-3-methylimidazolium hexafluoro phosphate and 531.9 g (2.05 mmol) tetrabutyl ammonium hydroxide were added respectively to the reactor to perform a next batch reaction. The reaction was repeated for 5 times continuously and the conversion of each batch is more than 99%.

Post-treatment for single batch reaction: 5 L of acetone was added to the reaction mixture liquid extruded out from the membrane reactor under stirring, and the product was separated out the mixture liquid and filtrated to get the crude product. Acetone was recycled by distilling the filtrate under reduced pressure and the residual ionic liquid was used in the next batch reaction after being saturated with water. The crude product was dissolved in 9 L of water/acetone (1/2) and recrystallized to get 318.9 g of white solid, wherein the separation yield was 90%, the ee value was 99.6% and the melt point was 241-243° C.

The NMR data of the compound 4 was as follows:

$^1$H NMR (DMSO-$d_6$, 400 MHz, δ ppm): 2.87 (m, 2H, $CH_2CH_2N$), 3.45 (m, 2H, $CH_2CH_2N$), 5.53 (d, 1H, CHCOOH), 7.35 (m, 4H, ArH), 9.45 (s, 1H, COOH).

EXAMPLE 3

Synthesis of (R)-Tetrahydroisoquinoline Methanol (Compound 5) Using the Following Reaction Scheme

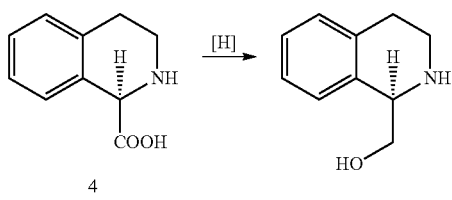

EXAMPLE 3-1

The compound 4 (17.72 g, 100 mmol) was added to 1000 ml tetrahydrofuran, hydrogen chloride was introduced into the solution, and the hydrochloride of compound 4 was obtained by evaporating and suspended in 1000 ml of tetrahydrofuran, the mixture was cooled to 0° C. and the solution of borane in tetrahydrofuran (300 mL, 300 mmol, 1M tetrahydrofuran solution) was added dropwise, and then the reaction was performed at 20-25° C. for 24 hours until the reaction system becomes clear. The reaction system was cooled to 0° C. and methanol (500 mL) was added, and 10% sodium hydroxide (70 mL) was added dropwise, and then the reaction mixture was performed at 20-25° C. for 4 hours. The organic solvent was evaporated off under reduced pressure and the residue was extracted with dichloromethane (200 mL). The organic phase was dried over anhydrous sodium sulfate, concentrated and recrystallized with toluene to get 15 g of white solid compound 5, wherein the yield was 92%, the purity was 96% and the melt point was 198-200° C.

The NMR data of compound 5 was as follows:

$^1$H NMR (CDCl$_3$, 400 MHz, δ ppm): 2.58 (s, br, 2H), 2.85-2.97 (m, 2H), 3.31-3.46 (m, 2H), 3.26 (br s, 1H, OH), 5.63 (dd, 1H), 7.35-7.78 (m, 4H, ArH). MS (ESI, +ve): m/z: 164.1 [M+H]$^+$.

EXAMPLE 3-2

The compound 4 (17.72 g, 100 mmol) was added to 1000 mL tetrahydrofuran, and sodium borohydride (3.8 g, 100 mmol) was added, and then the solution (20 mL) of boron trifluoride etherate was added dropwise, and the reaction mixture was stirred at 25-30° C. for 24 hours until the mixture becomes clear, the reaction mixture was cooled to 0° C., and methanol (500 mL) was added and 10% sodium hydroxide (70 Ml) was added dropwise at 0° C. When the addition was completed, the resulting solution was stirred at 20-25° C. for 4 hours. The organic solvent was evaporated off under reduced pressure and the residue was extracted with dichloromethane (200 mL). The organic phase was dried over anhydrous sodium sulfate, concentrated and recrystallized with toluene to get 15.5 g white solid of compound 5, wherein the yield was 95%, the purity was 98% and the melt point was 198-200° C.

The NMR data of compound 5 was as follows:
$^1$H NMR (CDCl$_3$, 400 MHz, δ ppm): 2.58 (s, br, 2H), 2.85-2.97 (m, 2H), 3.31-3.46 (m, 2H), 3.26 (br s, 1H, OH), 5.63 (dd, 1H), 7.35-7.78 (m, 4H, ArH). MS (ESI, +ve): m/z: 164.1 [M+H]$^+$.

EXAMPLE 4

Synthesis of Compound 11 Using the Following Reaction Scheme

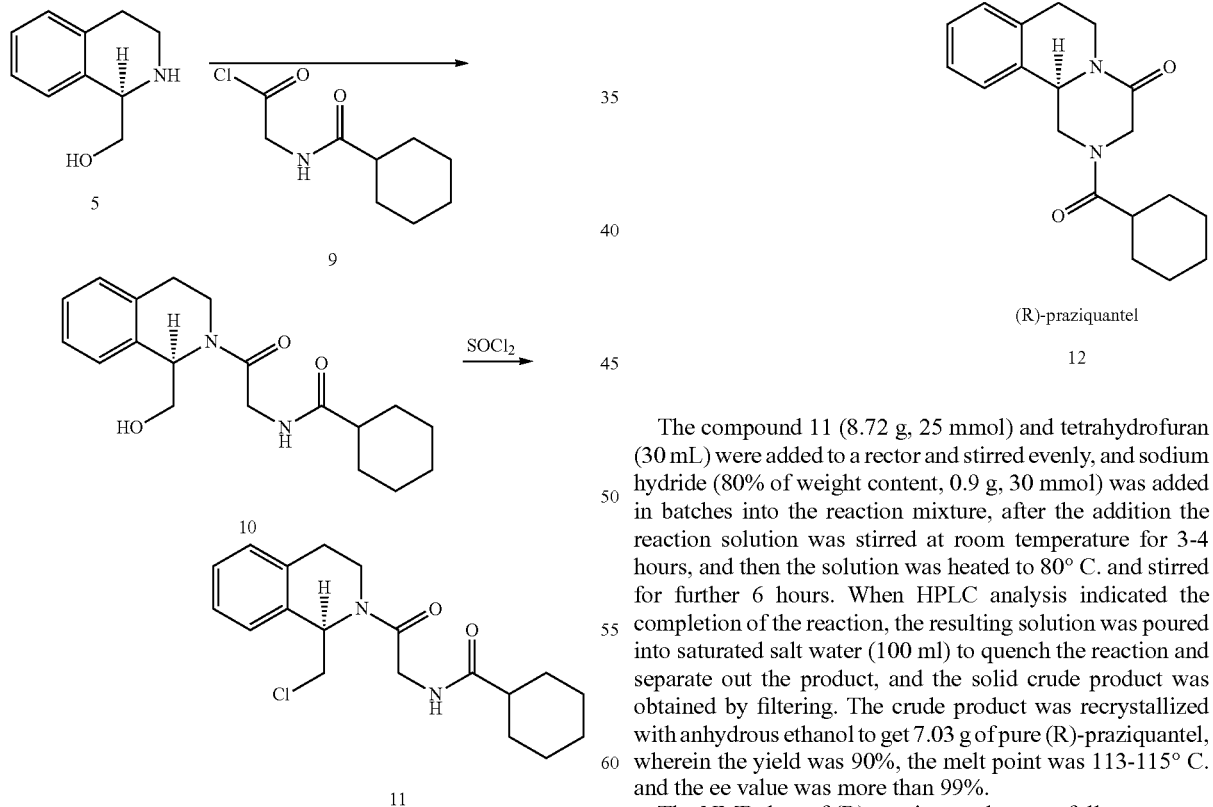

The compound 5 (8.16 g, 50 mmol), ethyl acetate (30 mL) and triethylamine (12.14 g, 120 mmol) were added to a reactor and stirred evenly, the compound 9 (cyclohexane carboxamide acetyl chloride, 12.22 g, 60 mmol) was added dropwise, subsequently the reaction mixture was stirred at room temperature for 3 hours. When HPLC analysis indicated the completion of the reaction, sulfoxide chloride (7.73 g, 65 mmol) was added, and the resulting mixture was heated so that the reaction was performed under reflux for 6-8 hours. When HPLC analysis indicated the completion of the reaction, the insoluble substance was filtered out, and the layer of ethyl acetate was washed with water and saturated salt water, and dried with anhydrous magnesium sulfate respectively, and the solvent was removed under reduced pressure to get solid crude product (13.95 g) of compound 11, the yield of was 80%, ee value was more than 99%, and the compound can be directly used in the next step.

EXAMPLE 5

Synthesis of (R)-Praziquantel (Compound 12)

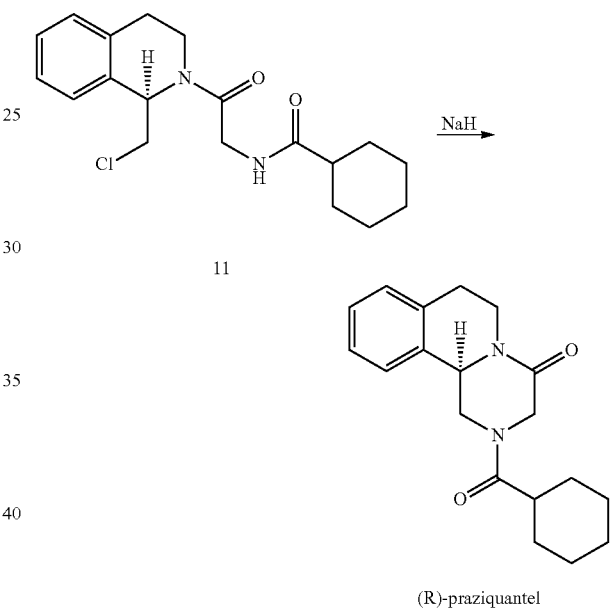

The compound 11 (8.72 g, 25 mmol) and tetrahydrofuran (30 mL) were added to a rector and stirred evenly, and sodium hydride (80% of weight content, 0.9 g, 30 mmol) was added in batches into the reaction mixture, after the addition the reaction solution was stirred at room temperature for 3-4 hours, and then the solution was heated to 80° C. and stirred for further 6 hours. When HPLC analysis indicated the completion of the reaction, the resulting solution was poured into saturated salt water (100 ml) to quench the reaction and separate out the product, and the solid crude product was obtained by filtering. The crude product was recrystallized with anhydrous ethanol to get 7.03 g of pure (R)-praziquantel, wherein the yield was 90%, the melt point was 113-115° C. and the ee value was more than 99%.

The NMR data of (R)-praziquantel was as follows:
1H NMR (DMSO-d6, 400 MHz, δ ppm): 1.21-1.96 (m, 10H, 5×CH$_2$), 2.45-2.50 (m, 1H, CH), 2.78-3.05 (m, 4H, CH$_2$), 4.10 (d, 1H, CH$_2$), 4.48 (d, 1H, CH$_2$), 4.79-4.85 (m, 2H, CH$_2$), 5.20 (d, 1H, CH), 7.12-7.30 (m, 4H, Ar—H).
MS (ESI, +ve): m/z: 313.1 [M+H]+.

The above embodiments are given for illustrating the technical concept or features of the invention, and this is intended to enable a person skilled in the art to appreciate the content of the invention and further implement it, and the protecting scope of the invention can not be limited hereby. Also, any equivalent variations or modifications made according to the spirit of the invention should be covered within the protecting scope of the invention.

What is claimed is:

1. A method for preparing (R)-praziquantel, comprising the following reaction scheme:

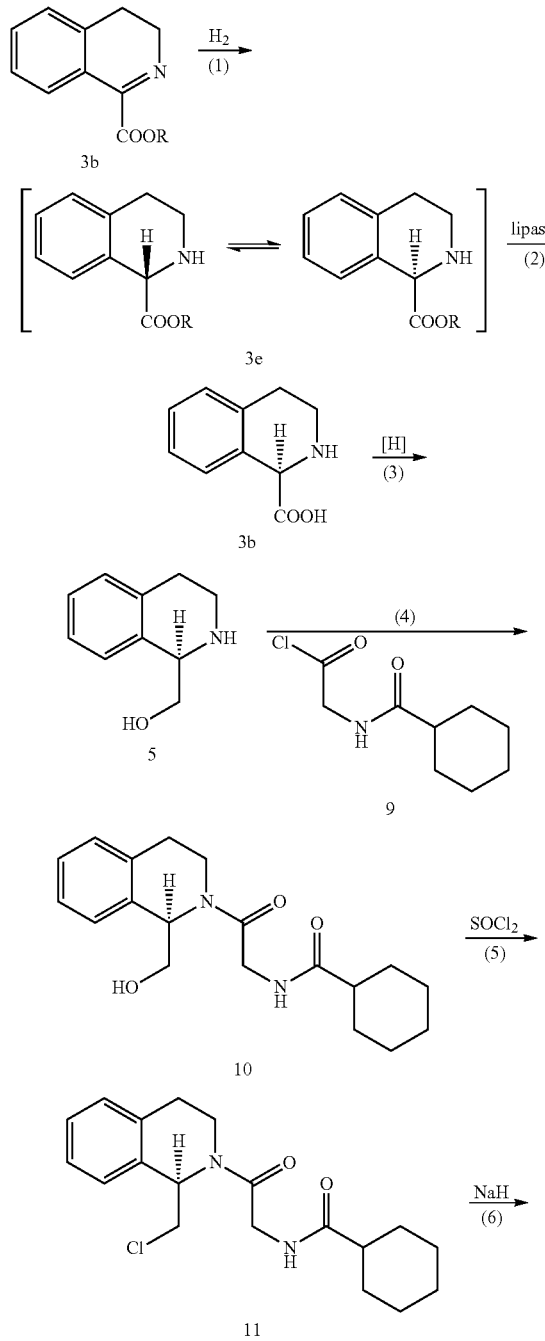

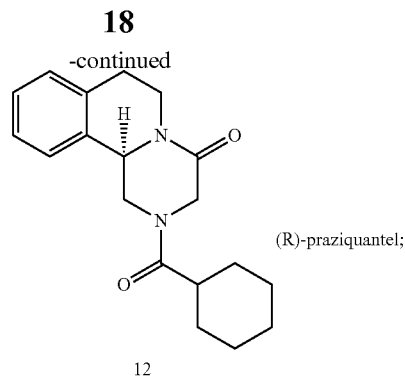

wherein

R represents alkyl; and wherein in step (2), the lipase stereo-selectively hydrolyzes a (R)-tetrahydroisoquinoline formate of the racemic compound 3e to obtain a pure optical (R)-tetrahydroisoquinoline formic acid having the structure of compound 4.

2. The method for preparing (R)-praziquantel as claimed in claim 1, wherein the lipase is selected from the group consisting of *Candida Rugosa* Lipase, *Candida Antarctica* Lipase A and *Candida Antarctica* Lipase B.

3. The method for preparing (R)-praziquantel as claimed in claim 1, wherein R is selected from the group consisting of methyl, ethyl, isopropyl, tert-butyl and p-methoxyphenyl.

4. The method for preparing (R)-praziquantel as claimed in claim 1, wherein the racemic compound 3e is reacted with the lipase in a water-saturated ionic liquid in the presence of a base at 0-50° C., to obtain compound 4.

5. The method for preparing (R)-praziquantel as claimed in claim 4, wherein the ionic liquid is selected from the group consisting of 1-n-butyl-3-methylimidazolium tetrafluoroborate, 1-n-butyl-3-methylimidazolium hexafluorophosphate, 1-n-butyl-3-methylimidazolium bis[(trifluoromethyl)sulfonyl]imide and 1-n-butyl-pyridinium hexafluorophosphate.

6. The method for preparing (R)-praziquantel as claimed in claim 4, wherein the base is selected from the group consisting of tetrabutyl ammonium hydroxide, pyridine, sodium bicarbonate, triethylamine and any combination thereof, and wherein the mole ratio of the base to the racemic compound 3e is in the range of 1-1.1:1.

7. The method for preparing (R)-praziquantel as claimed in claim 4, wherein the step (2) comprises:

adding the racemic compound 3e, the water-saturated ionic liquid and the base into a membrane reactor and stirring evenly;

adding the lipase to start the reaction under a sealed condition with HPLC monitoring the reaction; and extruding the components except the lipase in the reaction mixture out from the membrane reactor using a gas after the completion of the reaction, such that the lipase is retained in the membrane reactor for synthesizing a next batch of (R)-praziquantel.

8. The method for preparing (R)-praziquantel as claimed in claim 1, wherein the step (1) comprises:

reacting the compound 3b with $H_2$ in the presence of a Pd/C catalyst or a Raney nickel catalyst at 60-70° C. until the completion of the reaction; and recycling the catalyst by filtering and concentrating the filtrate under reduced pressure to get the racemic compound 3e.

9. The method for preparing (R)-praziquantel as claimed in claim 1, wherein the step (3) comprises:

suspending the compound 4 which is previously converted into its hydrochloride form or free form in tetrahydrofuran, and cooling the solution to 0-5° C.;

subsequently adding dropwise a solution of borane in tetrahydrofuran, or adding sodium borohydride first and then adding dropwise boron trifluoride etherate;

performing the reaction at 20-25° C. after the addition;

after the completion of the reaction, cooling the reaction mixture to 0-5° C. and adding methanol;

subsequently adding dropwise 10 wt %-15 wt % of sodium hydroxide at 0-5° C., heating the resulting mixture to 20-25° C. to perform neutralization reaction; and after the completion of the neutralization reaction;

evaporating off the organic solvent under reduced pressure;

subsequently extracting the residue with dichloromethane and drying the dichloromethane phase over anhydrous sodium sulfate and concentrating it to get crude product; and recrystallizing the crude product with toluene to get the compound 5.

10. The method for preparing (R)-praziquantel as claimed in claim 1, wherein the step (6) comprises:

adding compound 11 and tetrahydrofuran into a reactor and stirring evenly, adding sodium hydride in batches to the solution, stirring reaction mixture at room temperature for 3-4 hours, subsequently heating the mixture to 75-80° C. and further stirring for 5-7 hours with HPLC monitoring the reaction;

after the completion of the reaction, pouring the reaction mixture into saturated salt water to quench the reaction and separate out the product, subsequently filtering the solution to get crude product and recrystallizing the crude product with anhydrous ethanol to get (R)-praziquantel.

\* \* \* \* \*